(12) United States Patent
Gliner et al.

(10) Patent No.: US 10,182,904 B2
(45) Date of Patent: Jan. 22, 2019

(54) HEAT EXPANDABLE BREAST IMPLANT USING INDUCTION HEATING

(71) Applicant: Biosense Webster (Israel) Ltd., Yokneam (IL)

(72) Inventors: Vadim Gliner, Haifa (IL); Dganit David, Ahituv (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 15/438,205

(22) Filed: Feb. 21, 2017

(65) Prior Publication Data
US 2018/0235750 A1    Aug. 23, 2018

(51) Int. Cl.
| | |
|---|---|
| *A61F 2/12* | (2006.01) |
| *A61F 2/48* | (2006.01) |
| *A61L 27/50* | (2006.01) |

(52) U.S. Cl.
CPC ............ *A61F 2/12* (2013.01); *A61F 2002/48* (2013.01); *A61F 2210/0038* (2013.01); *A61F 2210/0061* (2013.01); *A61F 2230/0065* (2013.01); *A61F 2230/0071* (2013.01); *A61F 2230/0076* (2013.01); *A61F 2250/0001* (2013.01); *A61F 2250/001* (2013.01); *A61F 2250/0003* (2013.01); *A61F 2250/0004* (2013.01);
(Continued)

(58) Field of Classification Search
None
See application file for complete search history.

(56) References Cited

U.S. PATENT DOCUMENTS 2,542,619 A  *  2/1951  Bernhardt ................ A41C 3/10
                                                        521/145
6,146,418 A     11/2000  Berman
(Continued)

FOREIGN PATENT DOCUMENTS

| WO | 2011/086537 A2 | 7/2011 |
| WO | 2014/140282 A1 | 9/2014 |

OTHER PUBLICATIONS

Boud Minerals, "Expancel Microspheres—application guide—PVC Plastisol Printing Inks," Available at: https://web.archive.org/web/20160507142741/http://boud.com/sites/default/files/u27/boud_minerals—expancel_pvc_plastisol_printing_inks.pdf (May 7, 2016).
(Continued)

*Primary Examiner* — Andrew M Iwamaye
(74) *Attorney, Agent, or Firm* — Volpe and Koenig, P.C.

(57) ABSTRACT

A selectively expandable breast implant and method for tissue expansion are provided herein. The implant includes a flexible shell, an expandable material inside the flexible shell, and a plurality of closed conducting loops within the expandable material. The closed conducting loops absorb energy from a varying magnetic field external to the implant and generate heat, to heat the surrounding expandable material, and the expandable material expands in size based on the amount of heat generated by the closed conducting loops. The expandable material comprises a plurality of expandable microspheres that expands in response to the heat created by the closed conducting loops. The heat induction mechanism enables the closed conducting loops to generate heat for expansion of the expandable material in the implant. The implant can expand uniformly or in areas designated for selective shaping.

17 Claims, 6 Drawing Sheets

(52) U.S. Cl.
CPC . *A61F 2250/004* (2013.01); *A61F 2250/0008* (2013.01); *A61F 2250/0013* (2013.01); *A61F 2250/0015* (2013.01); *A61F 2250/0032* (2013.01); *A61F 2250/0043* (2013.01); *A61F 2250/0045* (2013.01); *A61F 2250/0047* (2013.01); *A61F 2250/0048* (2013.01); *A61F 2250/0059* (2013.01); *A61F 2250/0098* (2013.01); *A61L 27/50* (2013.01)

(56) References Cited

U.S. PATENT DOCUMENTS

| | | | |
|---|---|---|---|
| 6,605,116 | B2 | 8/2003 | Falcon et al. |
| 6,743,254 | B2 | 6/2004 | Guest et al. |
| 7,645,475 | B2 | 1/2010 | Prewett |
| 8,349,007 | B2 | 1/2013 | Berg et al. |
| 8,821,574 | B2 | 9/2014 | Davodian |
| 9,463,087 | B2 | 10/2016 | Hristov et al. |
| 2005/0192629 | A1* | 9/2005 | Saadat .................. A61F 5/0076 606/221 |
| 2005/0212630 | A1* | 9/2005 | Buckley ........... A61B 17/12022 335/35 |
| 2008/0199510 | A1* | 8/2008 | Ruane ...................... A61F 2/12 424/426 |
| 2009/0292306 | A1* | 11/2009 | Kheradvar ............ A61F 5/0036 606/192 |
| 2010/0010531 | A1 | 1/2010 | Shalon et al. |
| 2013/0116786 | A1 | 5/2013 | Sanabria Scharf |
| 2013/0150962 | A1* | 6/2013 | Sanabria Scharf ....... A61F 2/12 623/8 |
| 2015/0142098 | A1* | 5/2015 | Ruane ...................... A61F 2/12 623/1.15 |
| 2015/0327985 | A1 | 11/2015 | Hristov et al. |
| 2016/0262835 | A1 | 9/2016 | Davila et al. |

OTHER PUBLICATIONS

Comsol, "Induction Heating," Retrieved Mar. 6, 2017, from https://www.comsol.com/multiphysics/induction-heating.

Faraday's Law of Induction. In *Wikipedia*. Retrieved Feb. 27, 2017, from https://en.wikipedia.org/wiki/Faraday's_law_of_induction.

Halliday et al., "Fundamentals of Physics," $9^{th}$ Edition, Chapter 30, 30-5 Induction and Energy Transfers, pp. 797-798 (2010).

Induction Heating. In *Wikipedia*. Retrieved Feb. 27, 2017, from https://en.wikipedia.org/wiki/Induction_heating.

Klempner et al., "Principles of Operation of Synchronous Machines," in Operation and Maintenance of Large Turbo-Generators; Chaptef 1, pp. 3-32; John Wiley & Sons, Inc., Hoboken, NJ, USA. (2004).

Lenz's Law. In *Wikipedia*. Retrieved Feb. 27, 2017, from https://en.wikipedia.org/wiki/Lenz%27s_law.

Klempner et al., "Principles of Operation of Synchronous Machines," in Operation and Maintenance of Large Turbo-Generators, Chapter 1, pp. 3-32, John Wiley & Sons, Inc., Hoboken, NJ, USA. (2004).

* cited by examiner

HEAT EXPANDABLE BREAST IMPLANT USING INDUCTION HEATING

SUMMARY

Tissue expanders are devices that are implanted beneath a patient's skin, and then gradually inflated to stretch the overlying tissue. Such expanders are used to create an enlarged area under the skin for receiving a permanent prosthesis, or to generate increased skin surface area so that skin can be utilized for grafting or reconstruction.

Tissue expanders are typically used in conjunction with implantable devices, as an expander is a temporary device, which is ultimately replaced by a more permanent implant. Utilizing this process, two major surgical procedures are required: a first procedure to insert the expander and a second procedure to remove the expander and insert the more permanent implant. In the case of mammary implants, tissue expanders and implants are used for patients seeking aesthetic breast augmentation and for breast cancer patients requiring reconstruction following mastectomy. Current techniques for staged breast augmentation or reconstruction involve a first major surgery for the initial insertion of an expander, multiple subsequent "minor" procedures to inject saline or another fluid into the expander, followed by the final surgery to remove the expander and insert the more permanent implant.

Also, the multiple minor procedures to fill the expander with fluid are a source of anxiety and discomfort due to the pain and potential infection, inflammation and swelling. Thus, it would be advantageous to eliminate the need for multiple surgical procedures currently used for staged breast augmentation and reconstruction.

There is provided according to the described embodiments a medical apparatus including a selectively expandable permanent implant including a flexible shell, an expandable material inside the flexible shell, and a plurality of closed conducting loops within the expandable material. The plurality of closed conducting loops absorbs energy from an energy source external to the flexible shell and generates heat to heat the expandable material. The expandable material, which is located in close proximity to the closed conducting loops, heats up, thereby expanding in size, based on the amount of heat generated by the closed conducting loops. In one aspect, the expandable material comprises a plurality of expandable microspheres, wherein each microsphere comprises a polymer shell encapsulating an expandable gas. In another aspect, each closed conducting loop comprises a circular, electrically conductive metallic material.

Also provided herein is a method for tissue expansion utilizing an implant having a flexible shell containing an expandable material and a plurality of conducting loops, the method comprising exposing the implant to an energy source external to the implant, thereby causing the plurality of conducting loops to heat up; expanding the expandable material based on heat produced by the plurality of conducting loops; and removing the energy source on a condition that a desired expansion of the expandable material has been achieved.

These and other objects, features and advantages of the present invention will be apparent from the following detailed description of illustrative embodiments thereof, which is to be read in connection with the accompanying drawings.

DETAILED DESCRIPTION

Various embodiments of the invention are described in the following paragraphs. Where like elements have been depicted in multiple embodiments, identical or similar reference numerals have been used for ease of understanding.

Figure 1:
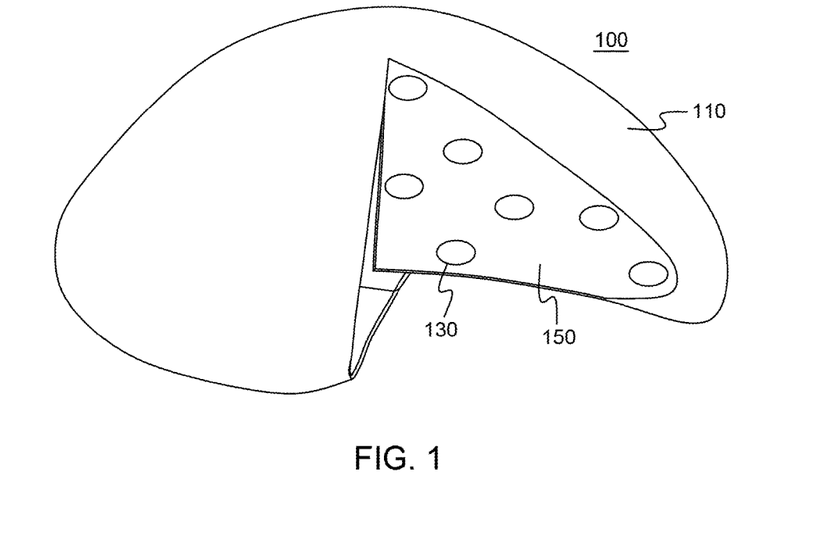
FIG. 1 is a cross-sectional view of an embodiment according to the invention.

Referring to FIG. 1, what is shown is an expandable implant 100 that eliminates most of the drawbacks associated with existing procedures, including a plurality of "minor" surgical procedures to inject an expander with fluid and the "major" surgical procedure to remove an expander and place an implant. Thus, the invention improves the staged breast augmentation and reconstruction processes and reduces the potential for complications due to infection, inflammation and pain.

Referring again to FIG. 1, a selectively expandable permanent implant 100 is shown, having a flexible silicon shell 110, which encases an expandable material 150 and a plurality of closed conducting loops 130 made of conductive material. In one embodiment, which will be referred to hereinafter as an example, the implant 100 is a permanent mammary implant. Additionally, although the implant 100 is referred to hereinafter as permanent, it may also be used as a non-permanent expander.

In one embodiment, the silicon shell 110 comprises a flexible biocompatible polymer. The shell 110 must be flexible in order to mimic the natural look and feel of a human breast. The shell 110 must also be strong to absorb physical shocks to the body without leaking or breaking.

Figure 2:
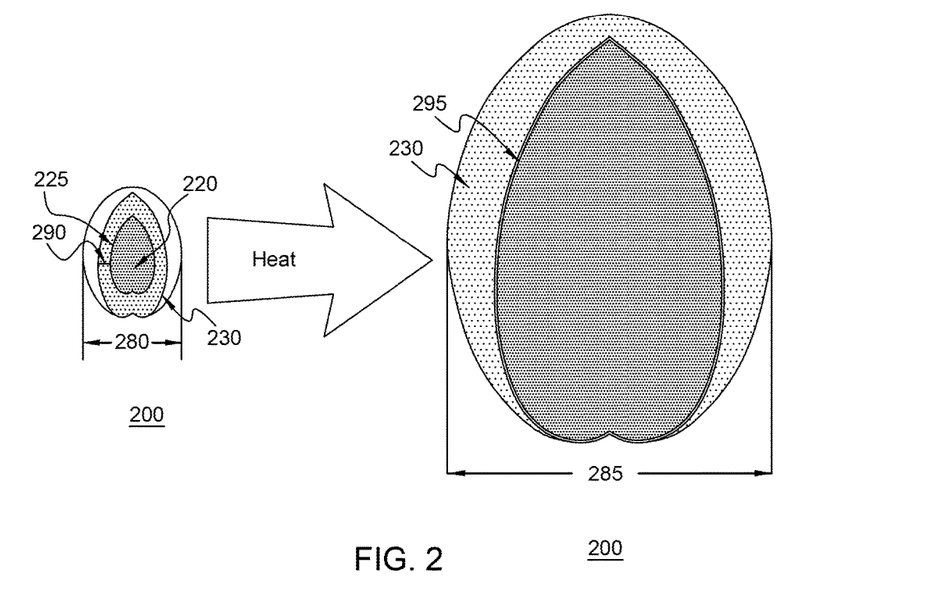
FIG. 2 is an illustration of the expandable material of the invention, showing how it expands when exposed to heat.

The expandable material 150 comprises a material which expands when it is heated to a certain temperature; (e.g. when a heating source is applied). In one embodiment, the expandable material 150 comprises, at least in part, a plurality of microspheres. Referring now to FIG. 2, a microsphere 200 in accordance with one embodiment is shown. Each microsphere 200 comprises a polymer shell 230, with a hollow core 220 having an outer surface 225, which encapsulates an expandable gas. In one embodiment, the expandable gas is hydrogen $H_2$ gas. When heat is applied to the microsphere 200, the expandable gas heats up, which causes the expandable gas to expand. This, in turn, causes the polymer shell 230 to expand. The polymer shell 230 features a variable width 290 around the polymer shell 230. The variable width 290 of the polymer shell 230 prior to expansion is greater than the width 295 of the polymer shell 230 after expansion. When the microsphere 200 is heated, the internal pressure from the expandable gas increases and the polymer shell 230 softens, resulting in a large increase of the volume of the microsphere 200. The gas remains inside the microsphere 200. The amount of expansion may be controlled by the amount of heat that is applied to the microsphere 200 within a certain time period. In one embodiment, the microspheres 200 comprise Expancel Microspheres from Boud Minerals, where the diameter 280 of the microsphere 200 prior to expansion is between 2 and 20 micrometers, and the diameter 285 of the microsphere 200 after expansion is between 12 and 100 micrometers. The microspheres 200 expand in size based on the amount of heat that is applied to them. In the embodiment shown in FIG. 1, the microspheres 200 comprise the entirety of the expandable material 150.

Once the heat is no longer applied, the microspheres 200 permanently retain their expanded size. This expansion is graphically illustrated in FIG. 2, where the left side is the microsphere 200 prior to expansion and the right side is the microsphere 200 after expansion.

Figure 3:
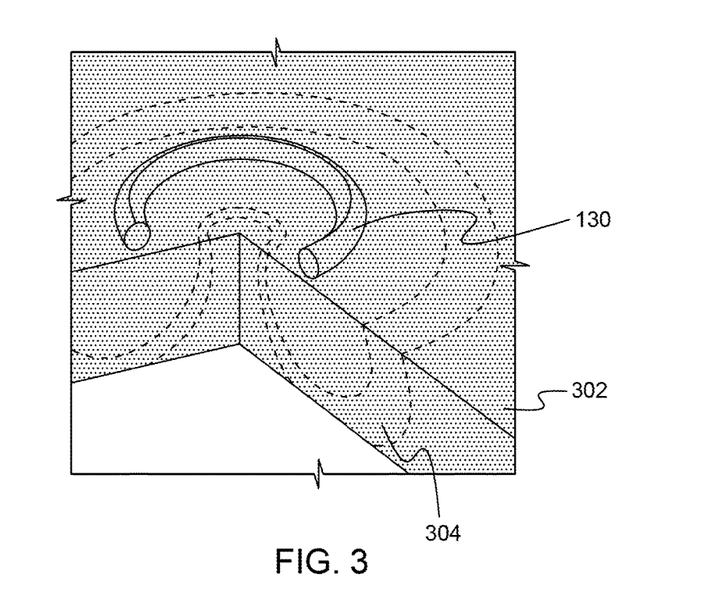
FIG. 3 is an example illustration of a closed conducting loop of the invention while it is generating heat due to its exposure to a varying magnetic field.

Referring to FIG. 3, each closed conducting loop 130 comprises a single loop of conductive metal. Although shown hereinafter as a single loop, the closed conducting loop 130 may have alternative shapes — any shape that permits a current to flow. A plurality of closed conducting loops 130 are mixed within the expandable material 150. Preferably, the closed conducting loops 130 are evenly mixed throughout the expandable material 150 such that there are an even distribution of closed conducting loops 130 and expandable material 150 throughout the implant 100. The closed conducting loops 130 are preferably in a high enough concentration, and spaced throughout the expandable material 150, such that the heat generated by the closed conducting loops 130 is enough to expand the surrounding expandable material 150.

The amount of heat generated by the closed conducting loops 130 depends on the level of change in magnetic flux through the closed conducting loops 130. The varying magnetic field (not shown) in which the closed conducting loops 130 are placed can produce a rapidly changing magnetic field, thereby creating changes in the magnetic flux through the closed conducting loops 130. With greater changes in the varying magnetic field, more heat will be produced by the closed conducting loops 130. Further, the closed conducting loops 130 may be small in diameter—up to 1 millimeter, for example. Even with such a small diameter, the closed conducting loops 130 will still produce sufficient heat to expand the adjacent expandable material 150. In one embodiment, the closed conducting loops 130 are all approximately the same size, so that each closed conducting loop 130 produces the same amount of heat. However, in an alternative embodiment, different sizes may be utilized.

Referring to FIG. 3, a closed conducting loop 130 is shown in greater detail. The closed conducting loops 130 comprise a material with high electrical conductivity, such as copper, gold, or aluminum. The closed conducting loop 130 shown in FIG. 3 is shown in a material 302 that is solid for simplicity of explanation. However, those of skill in the art would realize that the material 302 may comprise a plurality of microspheres 200 as shown in FIG. 2. When the closed conducting loops 130 are placed in a varying magnetic field (not shown), an electrical current is generated within the closed conducting loops 130. Since the closed conducting loops 130 are partially resistive, they heat up when a current is induced in them. The heat that is generated is transferred to the surrounding material 302, which begins to increase in temperature. This is graphically illustrated as heated material 304 in FIG. 3. As a result of the closed conducting loop 130 being placed in a varying magnetic field (not shown), a current is generated, the closed conducting loop 130 heats up, and transfers the generated heat to the surrounding material 302.

Figure 4:
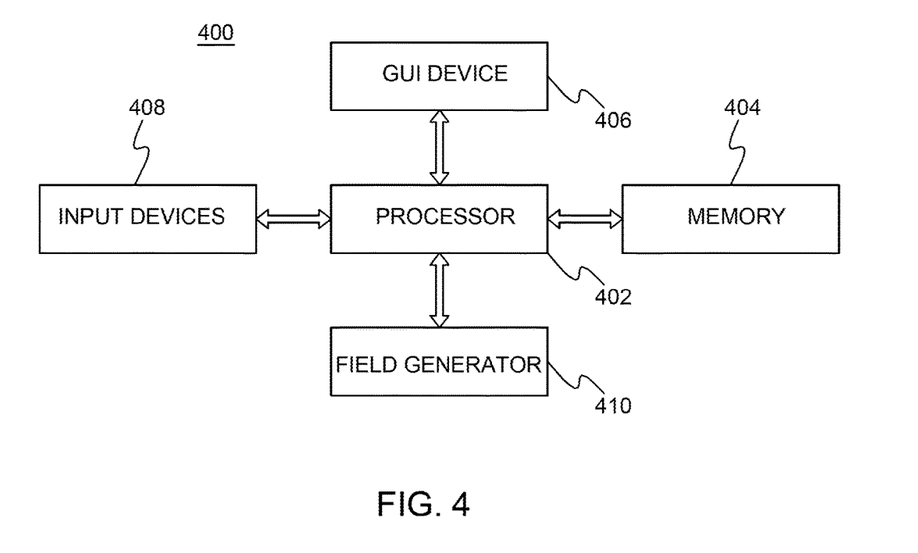
FIG. 4 is a block diagram of an example varying magnetic field generation system which is used in conjunction with one or more disclosed embodiments.

Referring to FIG. 4, a block diagram shows an example varying magnetic field generation system 400 in which one or more disclosed embodiments can be implemented. The varying magnetic field generation system 400 includes a processor 402, a memory 404, a graphical user interface ("GUI") device 406, one or more input devices 408, and a field generator 410. It is understood that the varying magnetic field generation system 400 can include additional components not shown in FIG. 4.

The processor 402 may include a central processing unit (CPU). The memory 404 can be located on the same die as the processor 402, or can be located separately from the processor 402. The memory 404 can include a volatile or non-volatile memory, for example, random access memory (RAM), dynamic RAM, or a cache.

The GUI device 406 uses a visual output for display. The GUI device 406 may also comprise a touch sensitive screen. The input devices 408 may include a keyboard, a keypad, a touch screen, a touch pad, a detector, a microphone, an accelerometer, a gyroscope, a biometric scanner, or a network connection (e.g., a wireless local area network card for transmission and/or reception of wireless IEEE 802 signals). The input devices 408 communicate with the processor 402, and the processor 402 receives input from the input devices 408. The field generator 410 emits a varying magnetic field, the power of which is controlled by the physician. This permits the physician to determine the amount of power to be applied to the closed conducting loops 130, and for how long, to ultimately attain the desired expansion of the microspheres 200 and the implant 100.

Figure 5:
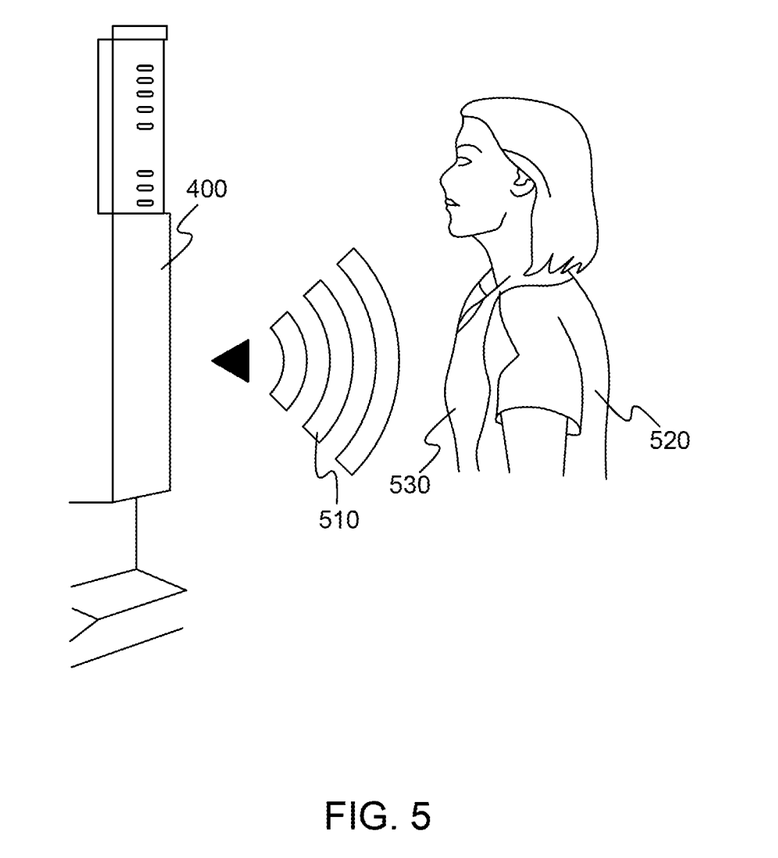
FIG. 5 is an example illustration of how the embodiments may be placed inside a varying magnetic field.

Referring to FIG. 5, the varying magnetic field generation system 400 is shown. The varying magnetic field generation system 400 emits a localized varying magnetic field 510 that changes rapidly—by as much as 10 Khz and above, for example—to produce significant magnetic flux changes in the closed conducting loops 130. The varying magnetic field generation system 400 is configured to comfortably accommodate a patient 520 having one or more breast implants 530. The varying magnetic field 510 that is generated passes though the implant 530. This generates the electric current within the plurality of closed conducting loops 130. Further, as $1/r^3$ is descriptive of the decrease in far-field magnetic strength, the power of the varying magnetic field 510 increases and decreases directly in relation to the proximity of the implant 530 to the varying magnetic field 510. As the implant 530 moves away from the varying magnetic field 510, the electric current produced within the closed conducting loops 130 of the implant 530 decreases.

As aforementioned, the closed conducting loops 130 heat up, and transfer heat to the surrounding expandable material 150. By utilizing a varying magnetic field 510, as shown in FIG. 5, the implant 530 uses a non-contact heating process, which is advantageous in view of the prior art methods that potentially cause infection and pain and anxiety during insertion of the needle for the expansion procedure.

Figure 6:
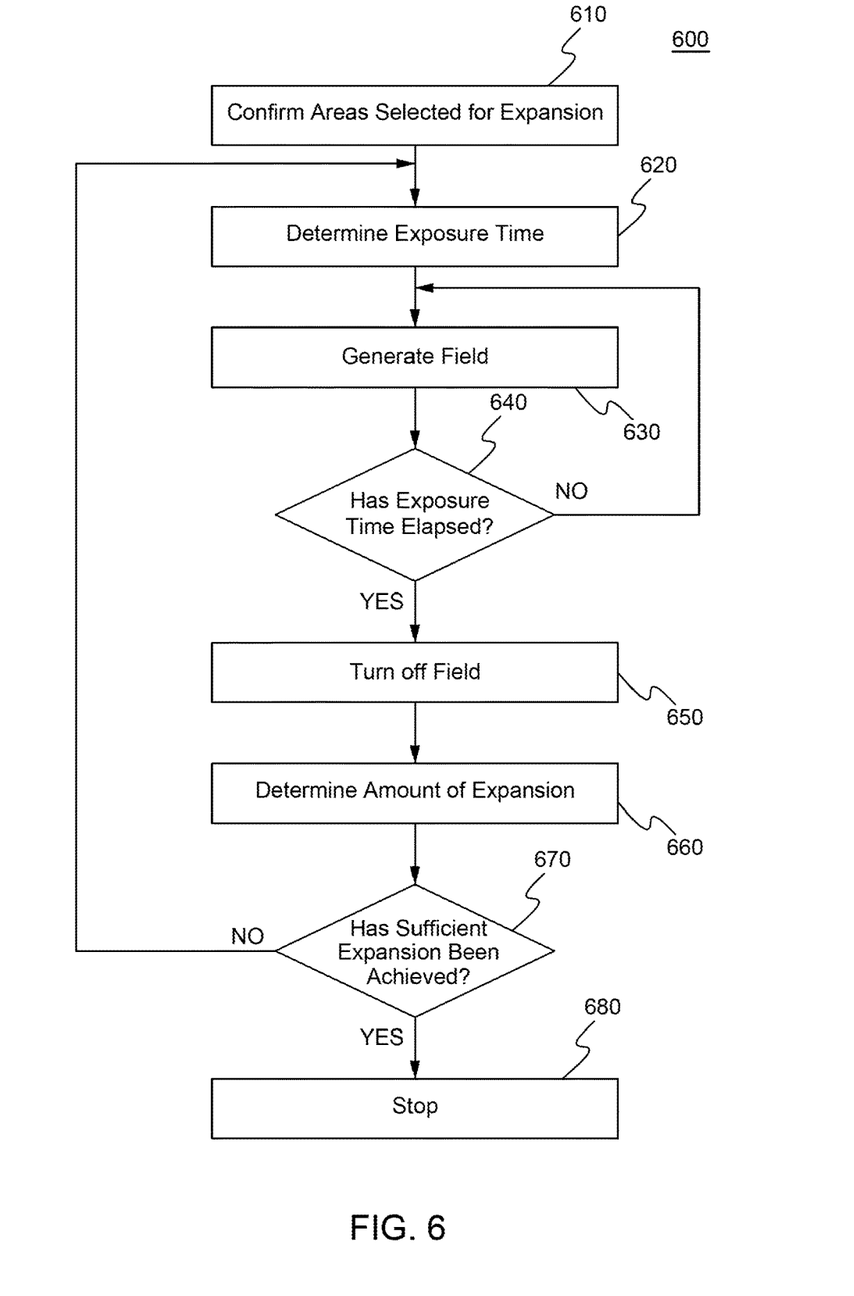
FIG. 6 is a flow diagram of an example procedure which is used in conjunction with the disclosed embodiments.

Referring to FIG. 6, a flow diagram illustrates the process 600 of expanding the implant 100 by utilizing a varying magnetic field generation system 400. As shown in FIG. 6, the process 600 begins 610 by confirming the areas that have been selected for expansion. A determination 620 is then made of the duration of exposure for the implant 100 to the varying magnetic field 510. The varying magnetic field generation system 400 will create the varying magnetic field 510 (step 630). After the implant 100 has been exposed to the varying magnetic field 510 for a certain amount of time, a determination will be made whether the exposure time has elapsed (step 640). If the implant 100 has completed the full duration of the allotted exposure time, then the varying magnetic field generation system 400 will deactivate the field (step 650). If the implant 100 still requires additional exposure time, then the varying magnetic field generation system 400 will again create the field (step 630) until the full, required exposure time has been completed. Upon completion of the full exposure time and after the field has been turned off (step 650), the implant 100 will be examined to determine the amount of expansion (step 660). A decision will be made as to whether sufficient expansion has been achieved (step 670). If sufficient expansion has been achieved, the process is complete (step 680). If further expansion is required, then the required amount of additional exposure time will be determined so that sufficient expansion can be achieved (step 620).

Figure 7:
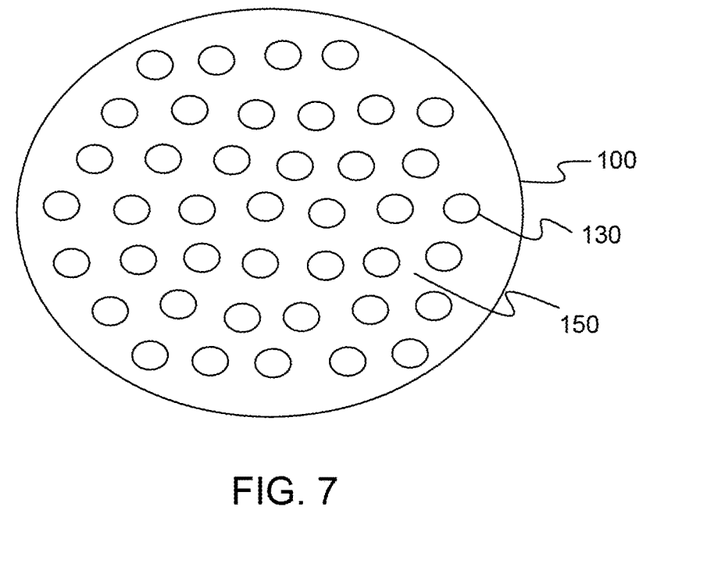
FIG. 7 is a cross-sectional view of an embodiment according to the invention, showing a uniform distribution of the closed conducting loops.

Referring to FIG. 7, a perspective view of this first embodiment is shown, where the closed conducting loops 130 are distributed evenly within the expandable material 150 to expand the implant 100 uniformly.

Figure 8:
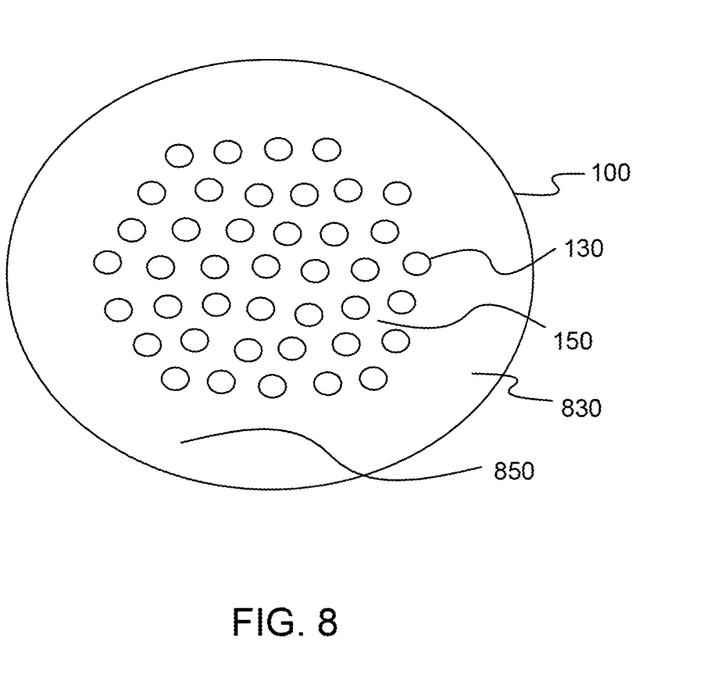
FIG. 8 is a cross-sectional view of another embodiment according to the invention, showing a uniform distribution of the closed conducting loops, where the implant has a perimeter buffer region, without the closed conducting loops.
Figure 9:
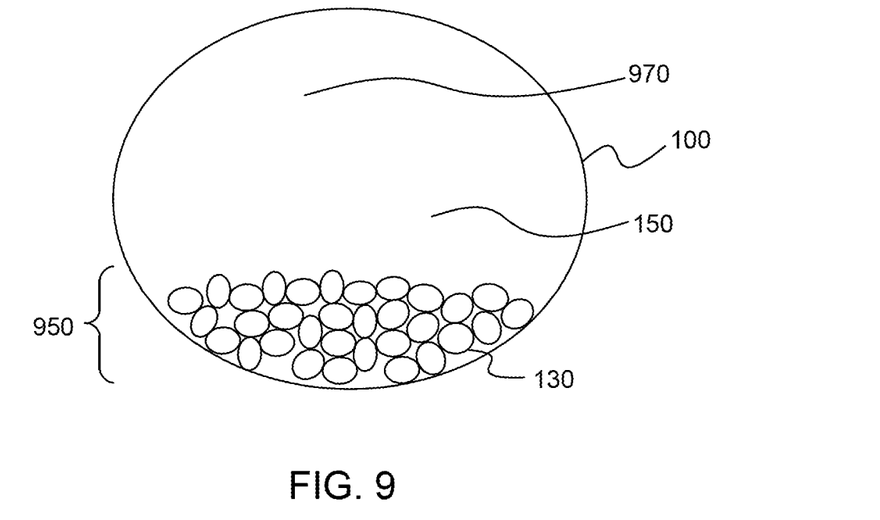
FIG. 9 is a cross-sectional view of another embodiment according to the invention, showing the implant having the closed conducting loops clustered closely together in a pre-determined area designated for shaping of the implant.
Figure 10:
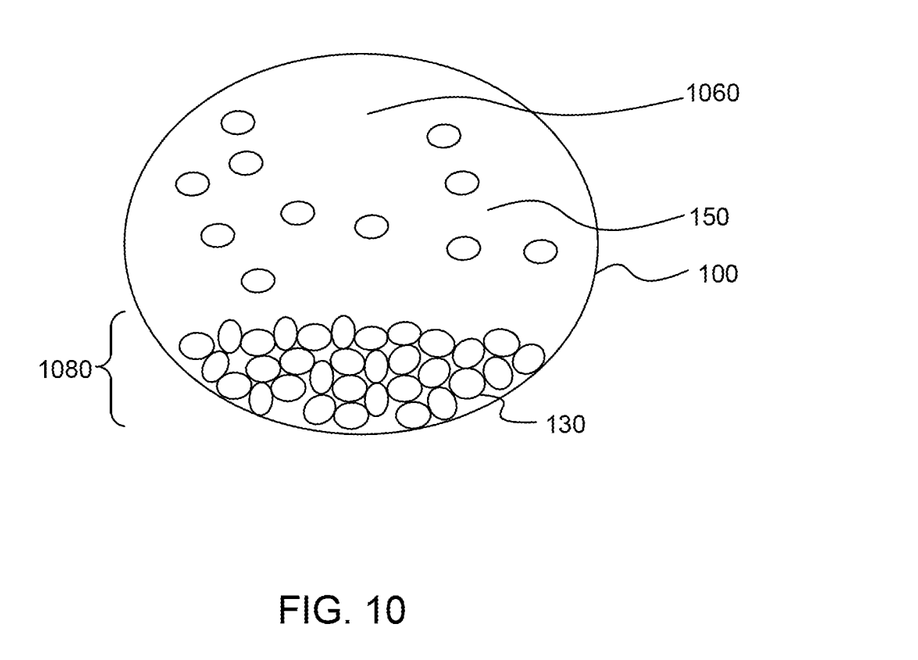
FIG. 10 is a cross-sectional view of another embodiment according to the invention, showing the implant having areas with a low distribution of the closed conducting loops and areas with a high distribution of the closed conducting loops.

FIGS. 8, 9 and 10 are illustrations of alternative embodiments of the implant 100. Referring to FIG. 8, a first alternative embodiment is shown. In this embodiment, the expandable implant 100 has a perimeter region 830 that is free of closed conducting loops 130. This affords protection as a buffer zone 850 around the circumference of the perimeter region 830 to the surrounding tissue against the elevated temperature of the closed conducting loops 130 within the implant 100.

Referring to FIG. 9, another alternative embodiment is shown, where the implant 100 has an un-even distribution of closed conducting loops 130 within the expandable material 150. Although the uneven distribution is shown as toward the bottom of the implant, the distribution may be selected to achieve any type of shaping or contouring that is desired. In the particular example shown, the implant 100 has closed conducting loops 130 clustered closely together in selected areas 950 within the expandable material 150 that are designated for shaping to contour targeted areas of the tissue. Notably, these selected areas 950 that are targeted for shaping may be located in the lower half of the implant 100, as shown in FIG. 9. This selectability in the expansion profile of the implant 100 permits the physician to tailor the expansion of the implant for different reasons. For example, selective expansion of the implant 100 may provide a remedy for sagging tissue. Further, the embodiment has pre-determined areas 970 within the expandable material 150 that are not designated for any shaping or expansion of the implant 100. In this pre-determined area 970, there are no closed conducting loops 130.

Referring to FIG. 10, another alternative embodiment is shown, where the implant 100 has an un-even distribution of closed conducting loops 130 within the expandable material 150. In particular, the implant 100 has areas with a low distribution 1060 of closed conducting loops 130 and areas with a high distribution 1080 of closed conducting loops 130. In the areas with low distribution 1060 of closed conducting loops 130, less expansion and shaping will occur. In the areas with high distribution 1080 of closed conducting loops 130, more expansion and shaping will occur. Notably, the areas with high distribution 1080 of closed conducting loops 130 may be located in the lower half of the implant 100, as shown in FIG. 10, to provide a remedy for sagging tissue, for example.

What is claimed is:

1. A selectively expandable breast implant comprising:
    a flexible shell;
    an expandable material inside the flexible shell; and
    a plurality of conducting loops within the expandable material;
    wherein the plurality of conducting loops absorb energy from an energy source external to the flexible shell and generate heat to heat the expandable material;
    wherein the expandable material expands in size based on the amount of heat generated by the plurality of conducting loops; and
    wherein the expandable material comprises a plurality of expandable microspheres.

2. The selectively expandable breast implant of claim 1, wherein each of the plurality of expandable microspheres comprises a polymer shell encapsulating a gas.

3. The selectively expandable breast implant of claim 1, wherein each of the plurality of conducting loops comprises a circular metallic element.

4. The selectively expandable breast implant of claim 1, wherein each of the plurality of conducting loops comprises an electrically conductive metallic material.

5. The selectively expandable breast implant of claim 1, further comprising a buffer region disposed between the flexible shell and the plurality of conducting loops, wherein the buffer region does not include any conducting loops.

6. The selectively expandable breast implant of claim 1, wherein the flexible shell comprises a round shape.

7. The selectively expandable breast implant of claim 1, wherein the flexible shell comprises a contoured shape.

8. The selectively expandable breast implant of claim 1, wherein the energy source comprises a varying magnetic field.

9. The selectively expandable breast implant of claim 1, wherein the plurality of conducting loops are unevenly distributed within the expandable material for selectable shaping of the selectively expandable breast implant.

10. A method for tissue expansion, the method comprising:
    providing an implant according to claim 1;
    exposing the implant to the energy from the energy source external to the flexible shell, thereby causing the plurality of conducting loops to heat up;
    expanding the expandable material based on heat produced by the plurality of conducting loops; and
    removing the energy from the energy source on a condition that a desired expansion of the expandable material has been achieved.

11. The method of claim 10, further comprising selecting an area of tissue for tissue expansion.

12. The method of claim 11, further comprising determining an amount of time for exposing the implant the energy from to the energy source external to the flexible shell.

13. The method of claim 12, wherein the exposing the implant to the energy from the energy source external to the flexible shell comprises generating the energy from the energy source by using a varying magnetic field generator.

14. The method of claim 13, further comprising determining whether the amount of time for exposing the implant to the energy from the energy source external to the flexible shell has elapsed.

15. The method of claim 14, further comprising deactivating the varying magnetic field generator when the amount of time has elapsed.

16. The method of claim 15, further comprising measuring the implant for an amount of expansion.

17. The method of claim 16, further comprising calculating whether the desired expansion of the expandable material has been achieved.

* * * * *